Aug. 4, 1970 MARIE-LOUISE MEILLAND Plant Pat. 2,986
ROSE PLANT
Filed July 1, 1968
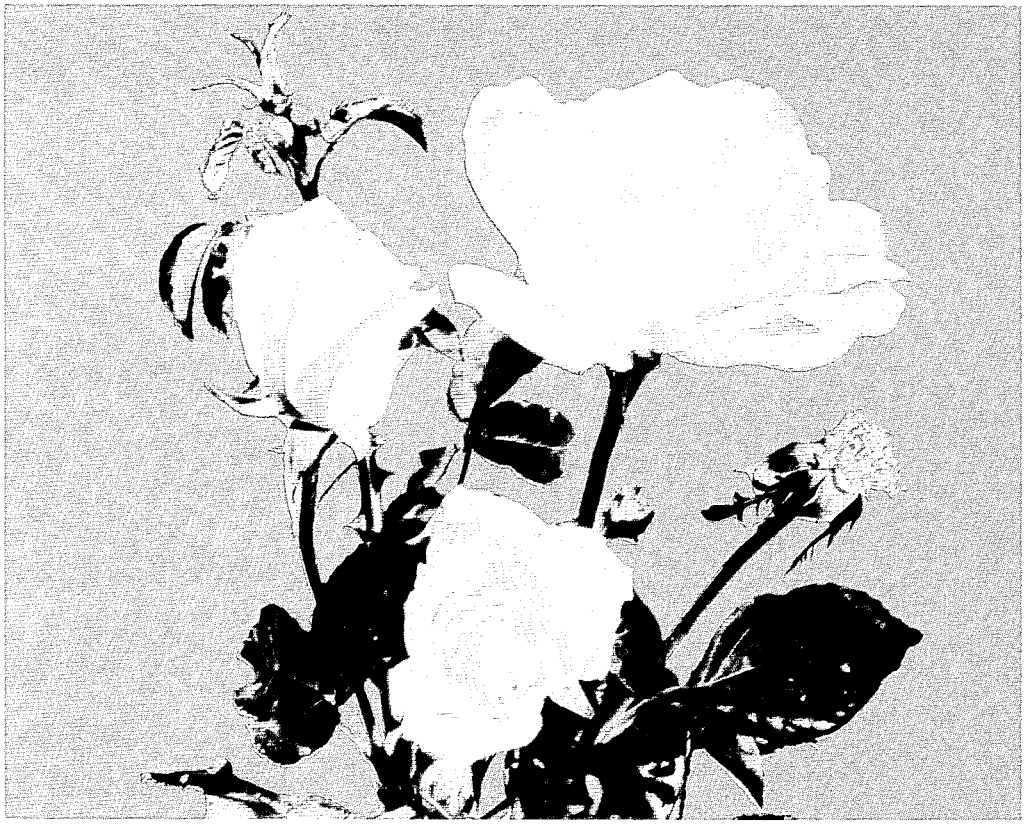

United States Patent Office

Plant Pat. 2,986
Patented Aug. 4, 1970

2,986
ROSE PLANT

Marie-Louise Meilland, Cap d'Antibes, France, assignor to The Conard-Pyle Company, West Grove, Pa., a corporation of Pennsylvania

Filed July 1, 1968, Ser. No. 741,808
Int. Cl. A01h *5/00*
U.S. Cl. Plt.—18 1 Claim

ABSTRACT OF THE DISCLOSURE

A new and distinct variety of rose plant of the hybrid tea class, originated by crossing an unnamed seedling resulting from a cross of Baccara and White Knight, with an unnamed seedling of the cross of Happiness × Independence with Better Times.

DESCRIPTION OF THE INVENTION

This invention relates to a new and distinct variety of rose plant of the hybrid tea class which was originated by crossing two unnamed seedlings.

The primary objective of this breeding was to create a distinct variety of rose different from all other known varieties of roses in several important characteristics.

The pollen parent of this rose is an unnamed seedling resulting from a cross of Baccara (Plant Pat. No. 1,367) with White Knight (Plant Pat. No. 1359) and characterized by its tall, erect and vigorous growth. The bud is pointed of Phlox Pink, opening to a large high centered bloom, also of Phlox Pink, with forty petals which become cupped when fully open.

This rose differs from its pollen parent by having deeper color in the bud and open bloom and on the average fewer petals.

The seed parent of this rose is an unnamed seedling of the cross (Happiness × Independence) with Better Times and characterized by a plant of medium height with upright habit and vigorous growth. The bud is ovoid of medium length and Deep Vermilion red. The full open bloom is flat and Light Vermilion Red with forty-five or more petals.

This rose differs from its seed parent by having a lighter color, fewer petals and more pointed bud form with petals of the open bloom loosely rolled outwardly. The bud and open bloom are larger than the seed parent. The plant is taller, more vigorous and more freely branched.

Asexual reproduction of my new variety by budding was performed in West Grove, Pa.

The accompanying drawing shows typical specimens of the flowers and foliage of my new variety in different stages of development and as depicted in color as nearly true as is reasonably possible to make the same in a color illustration of this character.

The following is a detailed description of my new variety with color terminology in accordance with the horticultural color chart of the Royal Horticultural Society:

Type: Hardy; tall bush outdoor; garden decoration; seedling.
Class: Hybrid tea.
Propagation: It holds its distinguishing characteristics through succeeding propagations by budding.

THE FLOWER

Flowers borne: Singly, sometimes three or four; irregular cluster; on strong, medium to long stems.
Quantity of bloom: Free, outdoors.
Continuity: Continuous.

Fragrance: Slight; sweetbriar.
Bud:
*Peduncle.*—Short; medium heavy; stiff; medium green; almost smooth; prickles brown.
*Before calyx breaks.*—Size—medium. Form—medium pointed with a conspicuous neck; with foliaceous appendages on the surface of the bud; with slender entire foliaceous parts entending beyond the tip of the bud equal to ¼ of its length.
*As calyx breaks.*—Color—Jasper Red 018/1.
*As first petal opens.*—Size—medium. Form—medium pointed. Color: outside—Porcelain Rose 620/1, Sap Green 62/3 at point of attachment; inside—Azalea Pink 618, Chartreuse Green 663/1 at point of attachment and along mid-vein in lower half of pedal.
*Opening.*—It opens up well. It is retarded from opening by cold wet weather.
Bloom:
*Size when fully open.*—Large, 4 to 5 inches.
*Petalage.*—Double; from thirty to forty petals; arranged regularly.
*Form.* High centered at first; becoming cupped; petals remaining at first loosely rolled outward; becoming later at maturity loosely rolled outward.
Petals: Medium soft; with inside satiny; outside velvety.
*Shape.*—Outer—round; with one notch. Intermediate—round to obovate; with one tooth.—Inner—obovate; no notches.

This description of a newly opened flower was made from a rose grown outdoors in June 1967, at West Grove, Pa.

*Color.*—Outer petal: outside surface—Carmine Rose 621/3, Chartruese Green 663/1 along lower ¼ mid-vein and point of attachment; inside surface—Empire Rose 0621, Chartreuse Green 663/1 at point of attachment. Intermediate petal: Outside surface—Carmine Rose 621/2, Chartreuse Green 663/1 at point of attachment. Inside surface—Empire Rose 0621, Chartreuse Green 663 at point of attachment. Inner petal: outside surface—Empire Rose 0621, Chartreuse Green 663/3 at very base of petal, Chartreuse Green 663 at point of attachment; inside surface—Delft Rose 020/1, Chartreuse Green 663 at point of attachment.

This description was made from a rose that was open for three days, outdoors in June 1967, at West Grove, Pa.

*Color.*—Outer petal: outside surface—Camellia Rose 622/2, Chartreuse Green 663/2 at point of attachment; inside surface—Carmine Rose 621/1, Chartreuse Green 663/1 at point of attachment. Inner petal: outside surface—Porcelain Rose 620/1, Chartreuse Green 663/3 at very base of petal, Chartreuse Green 663/1 at point of attachment; inside surface—Empire Rose 0621, Chartreuse Green 663/1 at point of attachment.
*General color effect.*—Newly opened flower—Carmine Rose 621/1. Three days open—Camellia Rose 622/1.
*Behavior.*—Drop off cleanly; colors deepen by cold weather.
*Flower longevity.*—On bush in garden five days in June; cut roses grown outdoors kept at living room temperatures 4 days in June.

REPRODUCTIVE ORGANS

Stamens: Medium; arranged irregularly about pistils occasionally.
Filaments: Many; most with anthers; medium long.

Color—Primrose Yellow 601/3.
Anthers: All open at once; medium large. Color—Naples Yellow 403. Seldom an anther fused with a pistil.
Pollen: Sparse; yellow.
Pistils: Medium.
Styles: Uneven; short to medium; very medium heavy; bunched.
Stigma: White.
Ovaries: All enclosed in receptacle.
Hips: None observed.
Sepals: Permanent; medium long; recurved.
Seeds: None observed.

PLANT

Foliage:

*Leaves.*—Five leaflets; normal; moderately large; heavy glossy.

*Leaflets.*—Shape—ovoid with apex acute, base obtuse, simply dentate.

*Color.*—Mature: upper surface—Parsley Green 00962 with maroon (general color term) at margins; under surface—Willow Green 000862/1. Young: upper surface—Willow Green 000862 shading to maroon (general color term) at margins; under surface—Willow Green 000862/3 overlaid with Erythrite Red 0027/1.

*Rachis (the supporting stem of the compound leaf).*—Medium. Upper side—smooth grooved. Under side—smooth.

*Stipules.*—Long; narrow; with medium long points; turning out at an angle of almost 90°; with red glandular tipped hairs.

*Disease.*—Resistance comparable to the average variety growing under the same cultural conditions.

Growth:

*Habit.*—Upright, much branched.

*Growth.*—Free.

*Canes.*—Heavy.

*Main stems.*—Dull; color—near Fern Green 0862/1. Prickles—several; color—Pod Green 061 sometimes shaded with maroon (general color term). Hairs—many; color—white (general color term).

*Branches.*—Dull; color—Lettuce Green 861/1. Prickles—several; color—Pod Green 061. Hairs—many; color—white (general color term).

*New shoots.*—Dull; color—Pod Green 061. Prickles—several; color—Sap Green 62. Hairs—several; color—most white, a few red glandular tipped.

I claim:

1. A new and distinct variety of rose plant of the hybrid tea class, substantially as herein shown and described, characterized particularly as to novelty by the unique combination of tall, vigorous growth, freely branched, upright plant habit; covered with large, heavy, glossy foliage of Parsley Green and freely producing a continuous quantity of bloom with medium large pointed buds of Porcelain Rose opening to a double bloom of Carmine Rose with petals loosely rolled outward, usually borne singly or occasionally two or three on sturdy, erect stems, and with disease resistance and hardiness characteristic of average varieties of the hybrid tea class.

No references cited.

ROBERT E. BAGWILL, Primary Examiner